US010787485B2

United States Patent
Beck-Sickinger et al.

(10) Patent No.: US 10,787,485 B2
(45) Date of Patent: Sep. 29, 2020

(54) PEPTIDE FOR COATING SURFACES (71) Applicant: Universität Leipzig, Leipzig (DE)

(72) Inventors: Annette Beck-Sickinger, Leipzig (DE); Mareen Pagel, Barcelona (ES); Rayk Hassert, Leipzig (DE)

(73) Assignee: Universität, Leipzig (DE)

( * ) Notice: Subject to any disclaimer, the term of this patent is extended or adjusted under 35 U.S.C. 154(b) by 0 days.

(21) Appl. No.: 15/759,055

(22) PCT Filed: Sep. 16, 2016

(86) PCT No.: PCT/EP2016/071958
§ 371 (c)(1),
(2) Date: Mar. 9, 2018

(87) PCT Pub. No.: WO2017/046323
PCT Pub. Date: Mar. 23, 2017

(65) Prior Publication Data
US 2019/0241614 A1    Aug. 8, 2019

(30) Foreign Application Priority Data
Sep. 17, 2015 (DE) .................. 20 2015 006 574 U (51) Int. Cl.
*A61K 47/64* (2017.01)
*A61L 27/34* (2006.01)
(Continued)

(52) U.S. Cl.
CPC ............. *C07K 7/06* (2013.01); *A61F 2/0077* (2013.01); *A61K 6/20* (2020.01); *A61K 47/60* (2017.08);
(Continued)

(58) Field of Classification Search
CPC .................. A61F 2/0077; A61F 2/0086; A61F 2002/3093; A61F 2310/00976;
(Continued)

(56) References Cited

U.S. PATENT DOCUMENTS

| 6,280,760 B1 * | 8/2001 | Meyer ................. A61L 27/34 424/422 |
| 7,662,190 B2 * | 2/2010 | Steinemann ........ A61F 2/30767 427/2.26 |

(Continued)

FOREIGN PATENT DOCUMENTS

| WO | WO 2008/150101 A2 | 12/2008 |
| WO | WO 2008/156637 A2 | 12/2008 |

OTHER PUBLICATIONS

Pagel et al. Multifunctional Coating Improves Cell Adhesion on Titanium by using Cooperatively Acting Peptides. Angewandte Chemie International Edition. 2016, vol. 55, pp. 4826-4830. Published online Mar. 3, 2016. (Year: 2016).*

(Continued)

*Primary Examiner* — Jeffrey E. Russel
(74) *Attorney, Agent, or Firm* — Curatolo Sidoti Co., LPA; Salvatore A. Sidoti; Floyd Trillis, III (57) ABSTRACT

The invention relates to a peptide comprising (i) a main chain comprising at least one L-3,4-dihydroxyphenylalanine (DOPA), (ii) at least one integrin binding peptide, and (iii) at least one heparin binding peptide. The invention further relates to a coating for metal surfaces comprising the peptide according to the invention and a coated metal surface which promotes osseointegration that can be obtained by reacting the peptide according to the invention with a metal surface.

16 Claims, 6 Drawing Sheets
(2 of 6 Drawing Sheet(s) Filed in Color)
Specification includes a Sequence Listing.

(51) Int. Cl.

| | | |
|---|---|---|
| *C07K 7/06* | (2006.01) | |
| *C07K 17/14* | (2006.01) | |
| *A61L 27/28* | (2006.01) | |
| *A61L 27/54* | (2006.01) | |
| *C07K 5/087* | (2006.01) | |
| *A61K 47/65* | (2017.01) | |
| *A61L 27/50* | (2006.01) | |
| *A61K 6/20* | (2020.01) | |
| *A61F 2/00* | (2006.01) | |
| *A61K 47/60* | (2017.01) | |
| *C07K 14/435* | (2006.01) | |
| *A61F 2/30* | (2006.01) | |

(52) U.S. Cl.
CPC .............. *A61K 47/64* (2017.08); *A61K 47/65* (2017.08); *A61L 27/28* (2013.01); *A61L 27/34* (2013.01); *A61L 27/50* (2013.01); *A61L 27/54* (2013.01); *C07K 5/0812* (2013.01); *C07K 14/43504* (2013.01); *C07K 17/14* (2013.01); *A61F 2002/3093* (2013.01); *A61F 2310/00976* (2013.01); *A61L 2300/25* (2013.01); *A61L 2300/606* (2013.01); *A61L 2400/18* (2013.01); *A61L 2420/00* (2013.01); *C07K 2319/00* (2013.01)

(58) Field of Classification Search
CPC ........ A61L 27/22; A61L 27/227; A61L 27/34; A61L 27/427; A61L 27/54; A61L 2300/25; A61L 2300/40; A61L 2300/606; A61L 2400/18; A61L 2420/00; A61L 2420/02; A61L 2420/04; A61L 2420/06; A61L 2420/08; A61K 47/62; A61K 47/64
See application file for complete search history.

(56) References Cited

U.S. PATENT DOCUMENTS

| | | | |
|---|---|---|---|
| 2005/0014151 A1* | 1/2005 | Textor | A61L 27/34 435/6.19 |
| 2009/0018642 A1* | 1/2009 | Benco | A61L 31/047 623/1.15 |
| 2013/0052712 A1 | 2/2013 | Cha et al. | |
| 2013/0224795 A1* | 8/2013 | Park | A61L 31/16 435/68.1 |
| 2018/0296727 A1* | 10/2018 | Reches | C07K 7/06 |

OTHER PUBLICATIONS

PCT/EP2016/071958—International Preliminary Report on Patentability, dated Mar. 20, 2018.
PCT/EP2016/071958—International Search Report, dated Dec. 6, 2016.
PCT/EP2016/071958—International Written Opinion, dated Dec. 6, 2016.
Rayk Hassert, et al., "Tuning peptide affinity for biofunctionalized surfaces", European Journal of Pharmaceutics and Biopharmaceutics, vol. 85, No. 1, pp. 69-77, Feb. 27, 2013, Elsevier.

* cited by examiner

Figure 1 mussel peptide (MP): C-Peg-Dopa-K-Dopa-Peg-Pra-βA (SEQ ID NO:8)

= c[RGDfK]     = FHRRIKA (SEQ ID NO:1)

integrin binding peptide (RGD)    heparin binding peptide (HBP)

MP-RGD-HBP

PEPTIDE FOR COATING SURFACES

This application is a national stage application under 35 U.S.C. § 371 of International Application No. PCT/EP2016/071958, filed 16 Sep. 2016, which claims priority from German Patent Application No. 20 2015 006 574.0, filed 17 Sep. 2015.

The present invention relates to a peptide, a coating, a coated implant as well as a peptide that can be obtained by combining solid phase synthesis and click chemistry.

Titanium (Ti) is the material of choice in the manufacture of dental implants and orthopaedic implants. However, as a result of lacking osseointegration inflammations, loosening, or sink in of the implant can occur. Osseointegration is the result of an osseous healing process in which the bone cells (osteoblasts) directly grow on to the implant and achieve a fixed attachment to the implant surface. In order to improve osseointegration of the implant it was tried to improve the bioavailability of the titanium surface by means of components of the extracellular matrix (ECM). Peptide coatings prepared of ECM components play an important role in the simulation of cell adhesive properties. Here, the best-known peptide is the integrin binding peptide RGD (Arg-Gly-Asp). Besides integrin binding peptides a binding to trans-membrane proteoglycans was shown for peptides with basic amino acids. It is assumed that the peptide sequence FHR-RIKA (Phe-His-Arg-Arg-Ile-Lys-Ala) (SEQ ID NO:1) binds to heparin-containing proteoglycans and thus, promotes attachment of cells. However, a direct immobilization of said molecules often is only possible after having functionalized the surface and requires integration of specific active groups into the peptide. It is known that the L-3,4-dihydroxyphenylalanine (DOPA) is able to bind to the oxidized surface of titanium without a chemical treatment. Said post-translationally modified amino acid was found in proteins that are secreted by the mussel (*Mytilus edulis*).

So, WO 2013/183048 A1 describes peptides having a titanium-binding amino acid sequence that is linked to a heterologous amino acid sequence. The titanium-binding amino acid sequence can contain L-DOPA and the heterologous amino acid sequence can contain an RGD motive.

Printed matter US 2013/0052712 A1 describes a scaffold that can contain an adhesive protein from *Mytilus edulis* and a bioactive substance. Variations of the mussel protein can contain L-DOPA and an RGD motive.

Synthesis and, in particular the specific covalent modification of recombinantly expressed mussel adhesion proteins with several bioactive molecules remain difficult.

Thus, it is the object of the invention to provide an effective modified molecule, which promotes osseointegration of implants, among others.

This problem is presently solved by a peptide comprising (i) a main chain having at least one L-3,4-dihydroxyphenylalanine (DOPA), (ii) at least one integrin binding peptide, and (iii) at least one heparin binding peptide. The combination of at least one DOPA, at least one integrin binding peptide, and at least one heparin binding peptide exhibits a synergistic effect in cell adhesion to metal surfaces coated with said peptide.

Here, the term main chain means any compound that can contain components of both peptidic and non-peptidic origin, as long as the main chain includes at least one L-3,4-dihydroxyphenylalanine (DOPA). Thus, the main chain can also contain non-peptidic components such as spacers, e.g. polyethylene glycol (PEG) spacers or amino hexanoic acid in addition to amino acids. Preferably, the main chain comprises at least two L-3,4-dihydroxyphenylalanines (DOPA). Preferably, the main chain is composed of at least 4 units that are linearly linked to each other, e.g. via peptide bonds. In a further preferred embodiment the main chain is composed of at least 5, at least 6, at least 7, or at least 8 linearly linked units. One, two, or three units are DOPA. At least 1, at least 2, at least 3, at least 4, or at least 5 units usually are amino acids.

It is further preferred that at least one unit is lysine. Moreover, the ε-amino group can covalently be bound to the integrin binding peptide or the heparin binding peptide. The main chain can contain 1, 2, or 3 lysines. Preferably, the integrin binding peptide is bound to a lysine.

Further, the main chain contains a unit to which the integrin binding peptide or the heparin binding peptide is covalently bound. In the peptide according to the invention a possible precursor of this unit is L-propargylglycine. The propargyl group is no longer contained in the peptide according to the invention, but has reacted by the coupling.

Further possible constitutes of the main chain or of the peptide according to the invention are β-alanine, PEG, aminohexanoic acid, and cysteine. The main chain can be amidated at the C-terminus.

In one embodiment the main chain is derived from a protein from the mussel *Mytilus edulis*. It is especially preferred that the main chain has the sequence Cys-PEG-DOPA-Lys-DOPA-PEG-L-propargylglycine-β-Ala-NH$_2$ (SEQ ID NO:2), wherein PEG represents polyethylene glycol. Without wishing to be bound to theory the PEG spacers are for increasing the solubility in aqueous media and reducing adhesion of proteins and bacteria.

Integrin binding peptide means any peptide that can bind to integrins. In a preferred embodiment the integrin binding peptide comprises the amino acid sequence Arg-Gly-Asp (RGD). Especially preferred is the cyclic amino acid sequence c[Arg-Gly-Asp-D-Phe-Lys] (cRGDfK).

Heparin binding peptide means any peptide that can bind to heparin. In a preferred embodiment the heparin binding peptide comprises the amino acid sequence Phe-His-Arg-Arg-Ile-Lys-Ala (SEQ ID NO:1).

In an exemplary embodiment the peptide has the following structure ("MP-RGD-HBP"):

MP-RGD-HBP

The above-described peptides excellently bind to metal surfaces, in particular to titanium. So, the peptides according to the present invention possess a binding affinity to metal surfaces, preferably to titanium, in which the saturation phase begins in the sub-μM range. In one embodiment, the binding affinity to metal surfaces, preferably to titanium, is in the range of 0.1 nM to 10 μM, preferably in the range of 1 nM to 1 μM, and especially preferred in the range of 10 nM to 100 nM.

Figure 2:
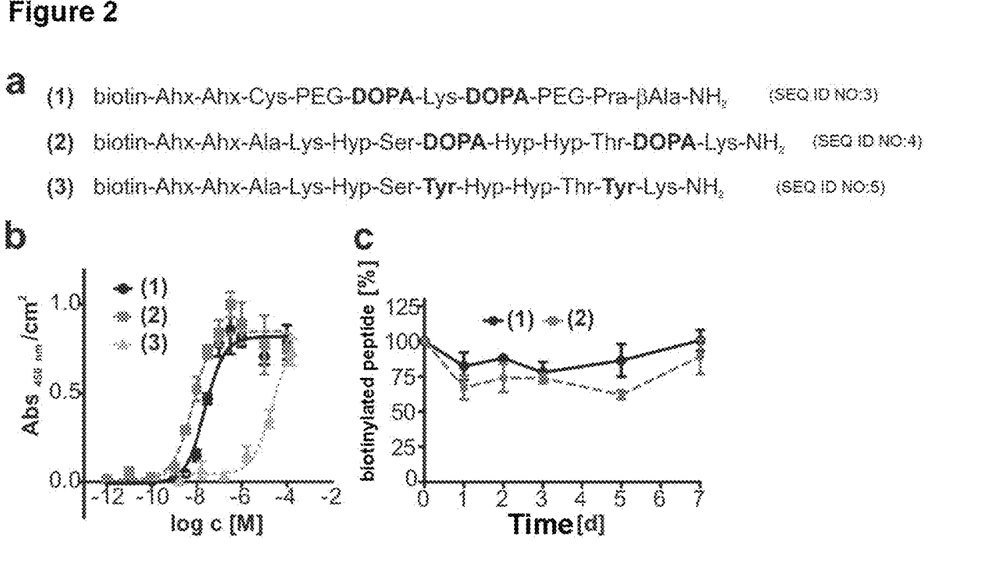
FIG. 2: Binding properties and stability of MP on titanium
(a) Sequence of the naturally derived (mefp-1) and of the artificial peptide (MP); Hyp (4-hydroxyproline), Ahx (amino hexanoic acid). (b) Concentration effect curve of the biotin ELISA in which there is apparent the saturation phase for MP and mefp-1 that begins in the sub-μM range. (c) Stability of the DOPA peptides on titanium incubated with cell supernatant at 37° (determined by a biotin ELISA).

Further, the peptides have an excellent stability. So, the peptides of the present invention are stable in aqueous solution at 37° C. over a period of time of at least week, preferably at least 2 weeks, especially preferred at least 4 weeks. Here, the term stable means that more than 50%, preferably more than 60%, preferably more than 70% of the peptide that is immobilized on the metal surface and biotinylated can be determined over this period of time (determination as performed in the examples, see FIG. 2C).

Moreover, the invention relates to a coating for metal surfaces, with the coating comprising a peptide as described above. The coating can contain further substances such as for example excipients and solvents.

In one embodiment the metal surface to be coated is of titanium.

In a further preferred embodiment the metal to be coated is implanted into a human or animal body. Here, any implant can be used. Preferably, the implant is selected from the list consisting of dental implants and orthopaedic implants, e.g. hip joint implants.

Moreover, the invention relates to a coated metal surface that can be obtained by reacting an above-described peptide with a metal surface. The coating can contain further substances, such as for example excipients and solvents.

In one embodiment the metal surface to be coated is of titanium.

In a further embodiment the metal to be coated is implanted into a human or animal body. Here, any implant can be used. Preferably, the implant is selected from the list consisting of dental implants and orthopaedic implants, e.g. hip joint implants.

Moreover, the invention relates to a coated implant that can be obtained by reacting an above-described peptide with an implant. Preferably, the implant is selected from the list consisting of dental implants and orthopaedic implants, e.g. hip joint implants.

Moreover, the present invention relates to a peptide comprising (i) a main chain comprising at least one L-3,4-dihydroxyphenylalanine (DOPA), (ii) at least one integrin binding peptide, and (iii) at least one heparin binding peptide, that can be obtained by combining solid phase synthesis and click chemistry.

Here, the term solid phase synthesis means the chemical synthesis of substances that are coupled to solid phases during the synthesis via covalently linking groups (so-called linker) to be released following synthesis by cleavage of the linker groups. For example, solid phase synthesis is carried out using the fluorenylmethoxycarbonyl/tert-butyl (Fmoc/tBu) strategy.

Here, the term click chemistry means the concept established by K. Barry Sharpless with Hartmuth C. Kolb and M. G. Finn which allows to rapidly and selectively synthesize target molecules from smaller units (Kolb et al., Angew. Chemie 2001, Vol. 113, p. 2056). Preferably, these are cycloaddition reactions, such as for example the Cu(I) catalyzed Huisgen cycloaddition (azide-alkyne cycloaddition) and the Diels-Alder reaction with inverse electron demand.

DESCRIPTION OF THE FIGURES

The patent or application file contains at least one drawing and photograph executed in color. Copies of this patent or patent application publication with color drawing(s)/photograph(s) will be provided by the Office upon request and payment of the necessary fee.

EXAMPLES

Titanium Binding Peptide (MP)

Figure 1:
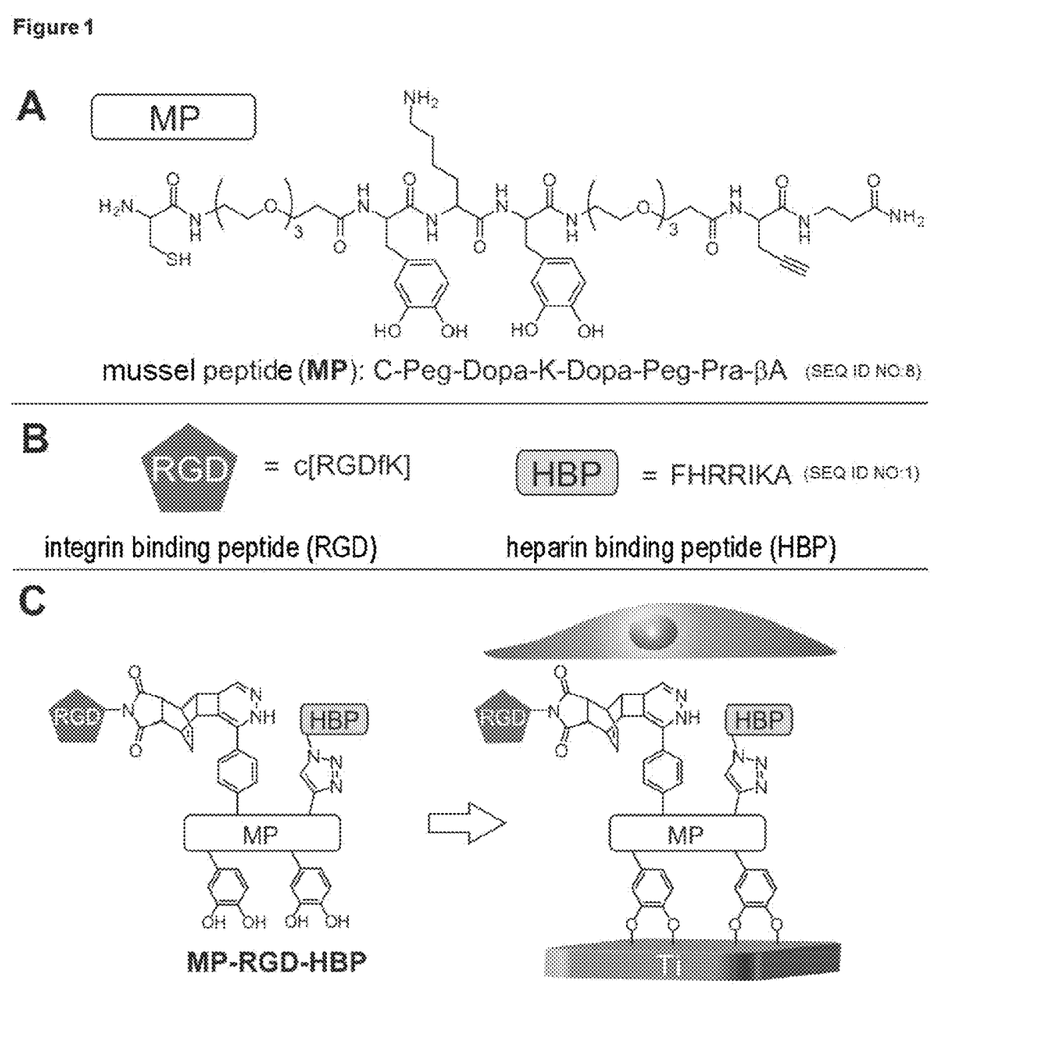
FIG. 1: Design of a multi-functional peptide
(A) Sequence of the titanium adhesive mussel peptide (MP); the peptide consists of the titanium binding amino acid (L-3,4-dihydroxyphenylalanine), functional groups introduced by Pra (L-propargylglycine), Cys and Lys as well as spacers such as PEG (polyethylene glycol) and β-Ala. (B) Cell binding peptides: cyclic integrin binding peptide (RGD), linear heparin binding peptide (HBP), (C) Ligation product consisting of MP, RGD, and HBP, synthesized by means of orthogonal cycloadditions (CuAAC and $DAR_{inv}$), and the resulting application of a "cell titanium adhesive".

In order to obtain a multi-functional titanium binding peptide a peptide from the mussel was designed that contains functional groups (FIG. 1A). Moreover, a PEG spacer was introduced, which on the one hand is to facilitate the following cycloaddition reactions and on the other hand increases aqueous solubility as well as reduces adhesion of proteins and bacteria.[1,2]

Following synthesis of the mussel peptide by solid phase peptide synthesis (Fmoc/tBu strategy) the binding affinity to titanium was studied. To study bound peptide by means of an already described biotin ELISA the peptides used were biotinylated at the N-terminus (two amino hexanoic acids were introduced as spacers).[3] As a positive control bio-(+) mefp-1 derived from the naturally occurring mussel foot protein sequence mefp-1 (M. edulis foot protein-1) was used to be able to assess the affinity to MP (FIG. 2A).[4] As the negative control the amino acid DOPA was replaced by tyrosine (bio-(-) mefp-1) to prove catechol mediated binding to titanium (FIG. 1C).

For that, titanium slices were etched in order to obtain a freshly oxidized surface. Subsequently, the titanium slices were incubated with various peptide concentrations. Following intensive washing steps titanium-bound peptide was identified with the well-described biotin-streptavidin interaction. Peptides containing DOPA showed high binding affinities with a saturation phase beginning in the sub-µM range (FIG. 2B). Here, the artificially designed peptide MP ($EC_{50}$=23.6 nM, $pEC_{50}$=7.6±0.1) binds with a similar affinity as the naturally derived mefp-1 peptide ($EC_{50}$=6.4 nM, $pEC_{50}$=8.2±0.1). Dramatically reduced adhesion properties were determined by the tyrosine peptide bio-(-) mefp-1 ($EC_{50}$>10000 nM, $pEC_{50}$=4.6±0.1). Moreover, stability of the DOPA peptides was tested in cell supernatant to imitate in vitro conditions. For that, titanium slices were coated with the corresponding biotinylated peptides (concentration=1 µM). Following incubation in SaOS-2 cell supernatant at 37° C. remaining peptide was identified by means of the biotin ELISA. Within a period of 7 days constantly more than 50% of immobilized and biotinylated peptide were detected (FIG. 2C). Moreover, no significant differences between artificial (bio-MP) and naturally derived peptide (bio-(+) mefp-1) could be found. However, MP showed a tendency to a higher stability.

Introducing Multi-Functionality—Bioorthogonal Cycloadditions to Solid Phase

Figure 3:
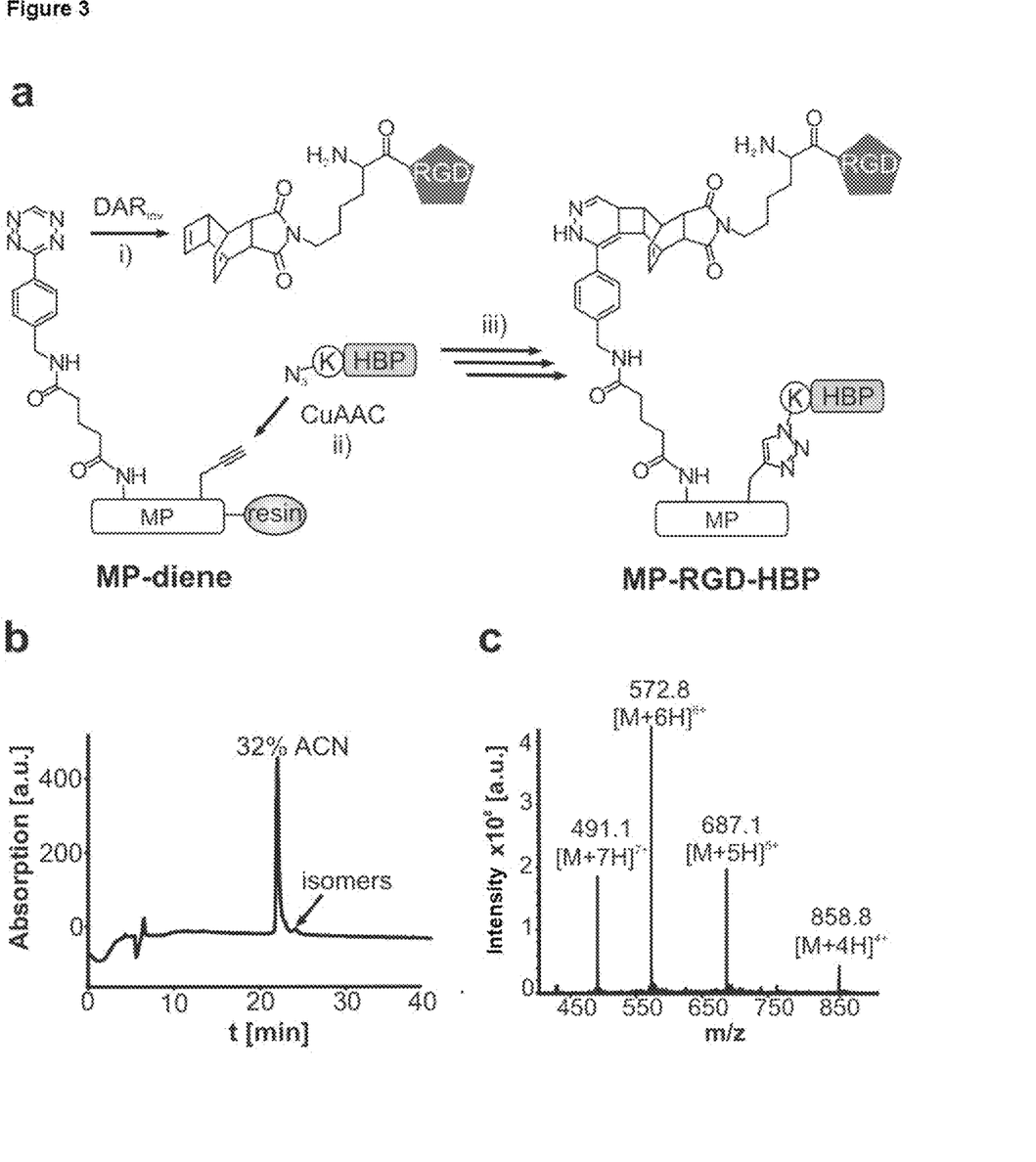
FIG. 3: Orthogonal cycloadditions on resin to obtain the multi-functional peptide MP-RGD-HBP
(a) Reaction scheme of $DAR_{inv}$ and CuAAC; Reagents and Conditions: a) water, RT, 5 h; b) $CuSO_4$, THPTA, TCEP in water, RT, 1d; after incubation with an aqueous EDTA solution the peptide was cleaved off from the resin with scavenger and TFA; (b) RP-HPLC chromatogram and (c) ESI ion trap MS of the purified MP-RGD-HBP.

Selective cell adhesion on inorganic surfaces can be mediated by various cell binding motives. By conjugating these motives with titanium binding peptides a cell surface mediator is formed. However, ligation of complex peptides, such as the cyclic $\alpha_v\beta_3$ selective ligands c[RGDfK] is particularly demanding. Thus, we developed a method that is compatible with the solid phase peptide synthesis that is based on the Diels-Alder reaction with inverse electron demand ($DAR_{inv}$) (a reaction between a diene and dienophile). Thus, the RGD peptide on the Lys side chain was modified with a dienophile (Reppe anhydride-lysine derivative). Accordingly, MP was modified with a tetrazine representing the diene. To perform $DAR_{inv}$ resin-bound MP diene was incubated with an aqueous solution of the c[RGD-fK(dienophile)] for 5 h. Then, the desired conjugate MP-RGD was cleaved off from the solid phase and could be identified by means of MALDI-ToF-MS and RP-HPLC. In addition to $DAR_{inv}$ orthogonal CuAAC was used to ligate a heparin binding peptide to MP-RGD. This was preceded by modifying MP with an alkyne group, introduced by propargylglycine, at the C-terminus. Accordingly, azido-lysine was coupled to HBP and subsequently cleaved off from the resin. Then, the purified peptide HBP-$N_3$ was used to perform CuAAC with resin-bound MP-RGD. Final cleavage of the ligated peptides showed that the desired product has formed in a yield of 75%. After purification the product and its corresponding isomers were analyzed with RP-HPLC and ESI-MS (FIG. 3C).

Cell Adhesion on Peptide-Coated Titanium

Figure 4:
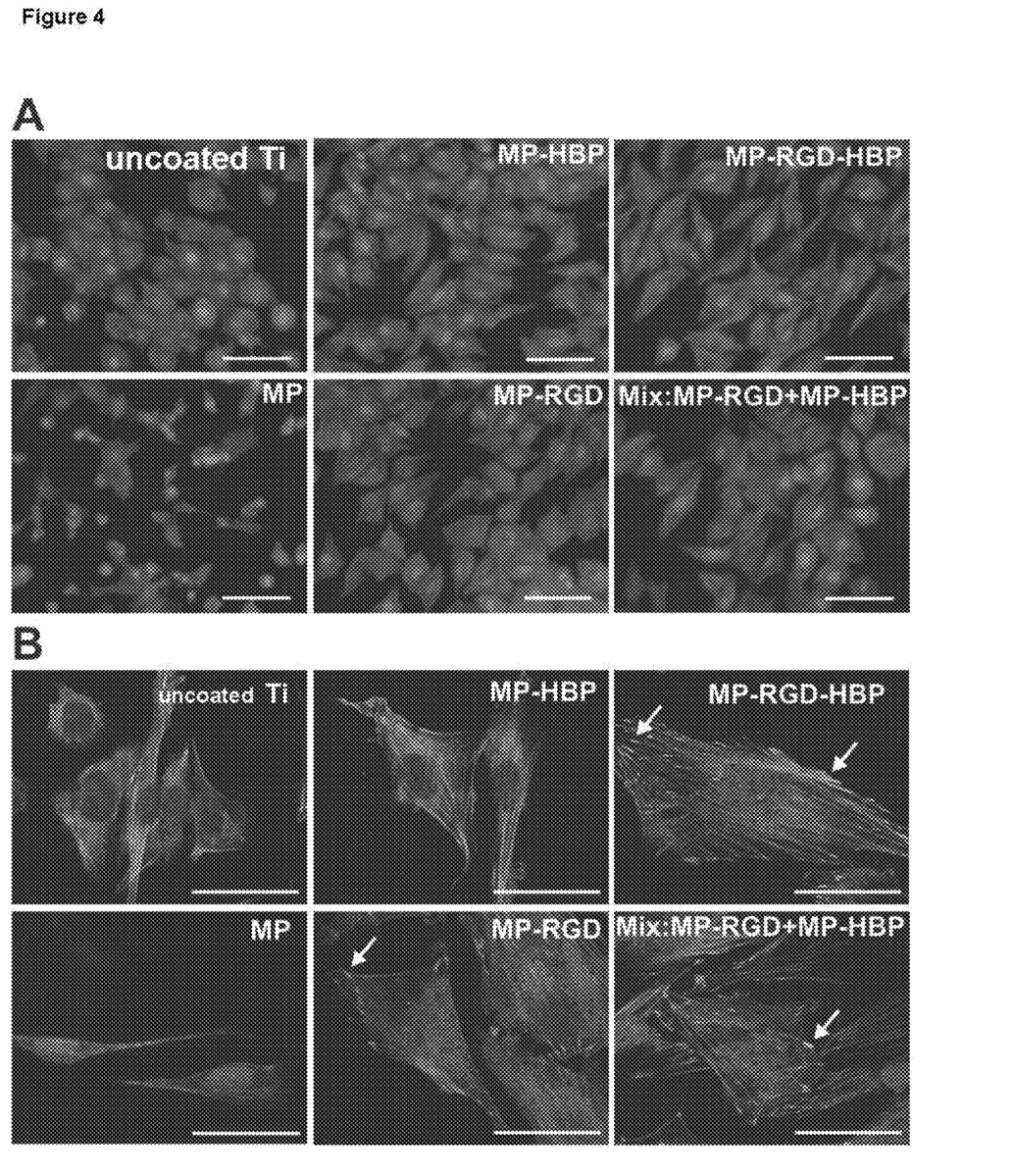
FIG. 4: Cell adhesion on peptide coatings in medium without FCS (fetal calf serum) Actin cytoskeleton red, nucleus blue and vinculin green (A) Fluorescence microscopy of SaOS-2 cells after 6 hrs. of adhesion on synthesized peptides and the negative control (uncoated Ti), scale: 100 μm (B) Immunolabelling of focal contacts: fluorescence microscopy images of SaOS-2 cells after 24 hrs. of adhesion on peptide coatings, scale bar: 50 μm.
Figure 5:
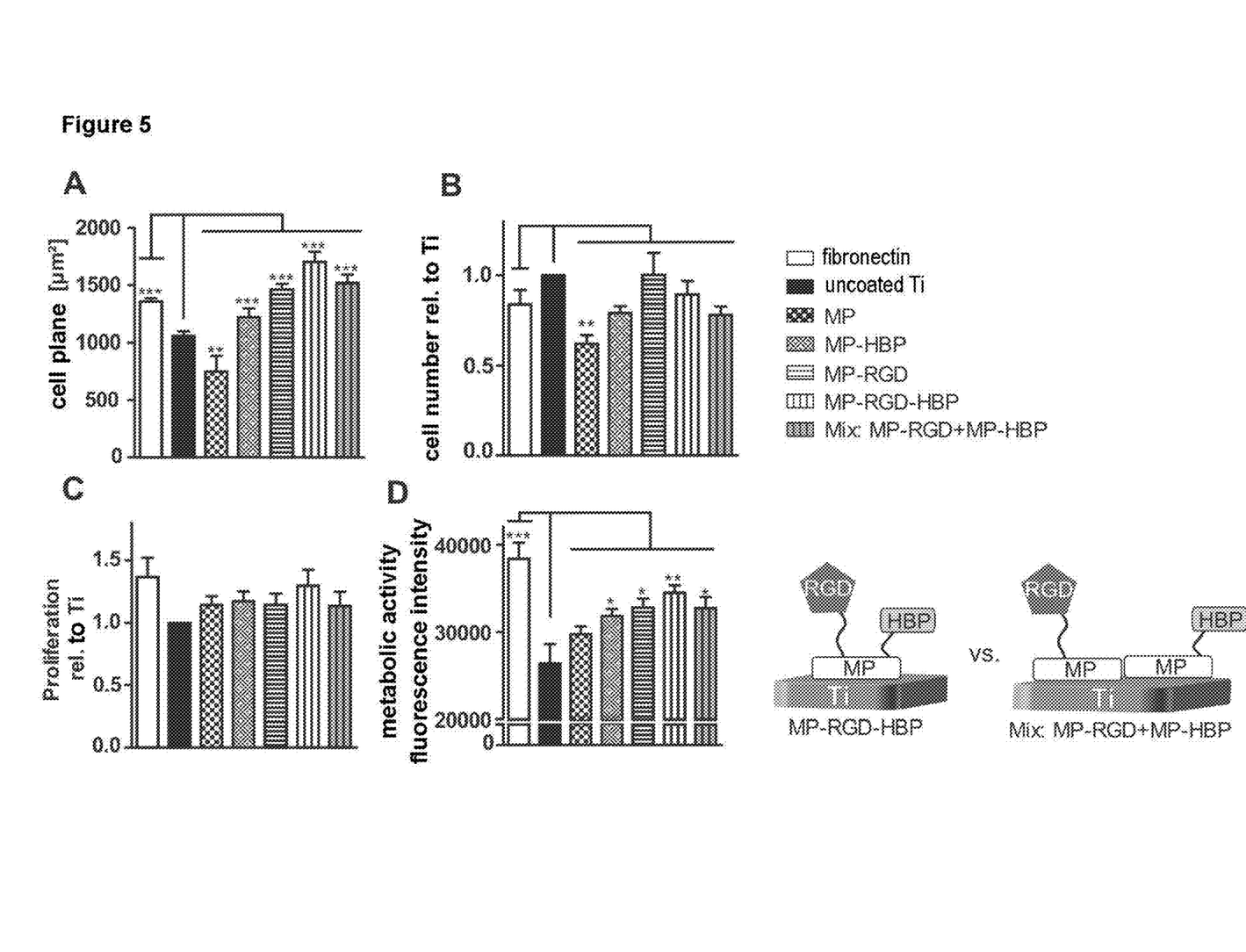
FIG. 5: Cell response to peptide coatings
A) average cell plane and B) cell count normalized to uncoated Ti=1 after 6 hrs. of adhesion in serum-free medium, determined by fluorescence microscopy. C) Proliferation (BrdU-assay, 24 h incorporation) normalized to Ti=1, and D) Viability (resazurin assay) after 3 days of cell adhesion (24 h in serum free medium, followed by FCS-containing medium). Results are expressed as mean±SEM from n≥3 (significant differences to uncoated titanium were determined by one-way ANOVA (***$p<0.001$)) diagram: multi-functional peptide versus mixture of single-modified peptides.

To determine the bioactivity of the ligated peptides and their controls cell adhesion studies have been performed. Osteoblast-like cells (SaOS-2) have been sown on etched peptide-coated titanium. All cellular experiments were performed in serum-free medium to prevent false results by adsorption of serum proteins. To study initial cell adhesion the cells were fixed and dyed after 6 h of cultivation to observe morphology and average cell plane and number by means of fluorescence microscopy. Here, the smallest cell propagation, determined on MP-coated titanium, became significant compared with uncoated titanium. Moreover, the cells showed a rather round shape with slightly formed cytoskeleton induced by the cell repellent properties of PEG.[5] To study this in more detail PEG was replaced by amino hexanoic acid. Indeed, an increase in cell size was observed, slightly higher than on uncoated titanium slices. Modification of MP with HBP resulted in an increase of cell propagation compared with MP and uncoated titanium. However, the cells only formed a few actin filaments and adhered in irregular cell shapes (FIG. 5A). Even better results could be achieved with an MP-RGD coating since an average cell size comparable to the naturally occurring ECM protein fibronectin could be found. Replacement of RGD with RAD resulted in a decrease of the cell size with a cell plane slightly higher than on uncoated titanium. Combination of HBP and RGD in a peptide induced the highest average cell plane, significantly compared with both controls (titanium, fibronectin), MP, MP-HBP, and MP-RGD. On the other hand, the mix of MP-HBP and MP-RGD resulted in no synergistic effect, since a cell propagation comparable to MP-RGD could be determined (FIGS. 4 and 5A). Cells having a fibroblast-like morphology and distinct bundles of fibrils have been found on all RGD-containing peptide coatings. Especially on MP-RGD-HBP distinctive, parallel actin filaments have formed (FIG. 4). In addition to the average cell plane the cell number was determined by counting cells that adhered after 6 h. Here, MP due to the cell repellent effect of the PEG mediated the smallest cell number, remarkably significantly less than on uncoated titanium (FIG. 5B). Moreover, a similar tendency as already in the cell plane experiment could be observed. Here, the cell number on RGD was increased to a greater extent than on HBP. Moreover, a mixture of RGD and HBP resulted in a smaller effect than RGD and HBP combined in a peptide. It is known that RGD peptides mediate the formation of focal contacts that are decisive for the outer-inner communication between cell and ECM.[6] By immuno-labeling with an anti-vinculin antibody it is possible to visualize vinculin, a protein involved in building up focal adhesion. Indeed, fluorescence microscopy images showed that line-like adhesion contacts (green) were formed on MP-RGD, MP-RGD-HBP and on the mixture: MP-HBP+RGD, mainly on the periphery of the cell (FIG. 4B). A slight increase in focal complexes could be observed on MP-RGD-HBP compared with singly modified RGD coatings. In contrast, MP, MP-HBP, and uncoated titanium resulted in the formation of a few or no focal adhesion contacts.

In addition to initial cell adhesion after 6 h cell viability and proliferation after 3 d was studied. Incorporation of the bromine-labeled thymidine analogue bromodeoxyuridine (BrdU) within 24 h, after 2 d of cell adhesion, was used to determine proliferation of cells on coated titanium. No significant changes could be found between the immobilized peptides and controls (FIG. 5C). However, a peptide coating is advantageous compared to untreated titanium. Moreover, a slightly increased cell proliferation on MP-RGD-HBP could be determined. Cell viability was studied after 3 days of adhesion by reacting resazurin to resorufin by living cells. All bioactively modified peptide coatings have a significantly improved cell viability compared to uncoated titanium. Even though MP mediated the smallest cell size and number, more living cells could be analyzed on this coating than on titanium. This fact emphasizes the cell repellent, but at the same time not toxic properties of the PEG. In particular, MP-RGD-HBP leads to the best result among all synthesized peptides. MP-RGD induces a similar cell viability like a mixture of MP-RGD and MP-HBP. Thus, the advantageous approach to present both cell binding peptides in one molecule is confirmed.

Experimental Part

Materials and Methods

Fmoc-protected amino acids and reagents for peptide synthesis were obtained from Novabiochem, IrisBiotech, Sigma Aldrich, Roth, Bachem and Orpegen OPC. Solvents were bought from Biosolve and VWR. The dienophile Reppe anhydride-lysine derivative was synthesized as described elsewhere.[7] The tetrazine 5-[4-(1,2,4,5-tetrazine-3-yl)benzyl-amine]-5-oxopentanoic acid was bought from Sigma Aldrich. Reagents for cuprous-catalyzed azide-alkyne cycloaddition (CuAAC) were provided by Sigma Aldrich. Cell culture material was obtained from PAA, Lonza, and Biochrome.

Synthesis of the Heparin Binding Peptide (HBP) and Mefp-1 Peptide Variants

HBP and mefp-1 (*Mytilus edulis* foot protein-1) derived peptides were prepared by means of automated solid phase peptide synthesis (Syro peptide synthesizer, MultiSynTech) on Rink amide resin (15 μmol, loading 0.7 mmol/g) with standard fluorenylmethoxycarbonyl/tert-butyl (Fmoc/tBu) strategy. A detailed protocol is described by Bohme et al.[8] The unnatural amino acid Fmoc-Lys($N_3$)—OH was manually coupled to the N-terminus of HBP with 2 eq 1-hydroxybenzotriazole (HOBt) and diisopropylcarbodiimide (DIC) in dimethylformamide (DMF) for 4 hrs. Peptides used for biotin ELISA were modified at the N-terminus with two units of Fmoc-Ahx-OH and finally with biotin by HOBt/DIC activation.

Synthesis of the Mussel Peptide (MP)

Mussel derived peptides were manually synthesized on TentaGel S RAM (IrisBiotech). Deprotection of the α-amino group was performed twice with 30% (v/v) of piperidine in DMF for 10 min. Subsequently, the following amino acids were equimolarly coupled with 2 eq HOBt/DIC in DMF: Fmoc-β-Ala-OH, Fmoc-Pra-OH, Fmoc-DOPA(acetonide)OH, Fmoc-Lys(Mtt)-OH, Fmoc-Ahx-OH, Fmoc-Cys(Trt)-OH. For activating the amino acid derivative Fmoc-NH-$(PEG)_2$-COOH (13 atoms) 1.5 eq of O-(7-azabenzotriazole-1-yl)-N,N',N'-tetramethyluronium-hexafluorophosphate (HATU) and equimolar amounts of diisopropylethylamine (DIPEA) were used. Selective cleavage of the protecting group 4-methyltrityl (Mtt) was performed with 2% of trifluoroacetic acid (TFA), 3% of triisopropylsilane (TIS) in dichloromethane (DCM) (v/v/v). Subsequently, the diene 5-[4-(1,2,4,5-tetrazine-3-yl)benzyl-amino]-5-oxopentanoic acid was coupled in double surplus with HOBt/DIC for 16 hrs.

Biotinylation of the MP was performed as already described.

Synthesis of the c[RGDfK(Dienophile)]

The cyclic RGD peptide was synthesized as described in Hassert et al.[3]

Diels-Alder Reaction with Inverse Electron Demand ($DAR_{inv}$) on the Solid Phase TentaGel resin loaded with the diene-modified mussel peptide was swollen in water. Subsequently, the resin was incubated with an aqueous solution of the c[RGDfK(dienophile)] (1.5 eq, 30 mM) for 5 hrs. at room temperature on a shaker in an open reaction vessel ($N_2$ release). Following washing steps with water, DMF, and DCM Fmoc was cleaved off from the N-terminus. Finally, the peptide was cleaved off from the resin.

Cuprous-Catalyzed Azide-Alkyne Cycloaddition (CuAAC) on Solid Phase

TentaGel resin loaded with MP or MP-RGD, respectively was swollen in water. For modification of MP 2 eq. of $CuSO_4.5H_2O$ (10 mM), 4 eq. of tris(2-carboxyethyl)phosphine (TCEP, 0.1 M), and 0.2 eq. of tris[(1-benzyl-1H-1,2,3-triazol-4-yl)methyl]amine) (TBTA) in $H_2O$/acetonitrile (ACN) (3:2, 2 mM) were mixed, degased with Ar, and incubated for 15 min. at 37° C. Subsequently, 1 eq. of the HBP—$N_3$ peptide was added to the mixture and the pH value was adjusted to pH 8 with an aqueous NaOH solution (10 mM). After the resin was incubated with the reaction mixture all was degased again with Ar and shook for 44 hrs. at 37° C. For the modification of MP-RGD a mixture of eq. of $CuSO_4.5H_2O$ (0.1 M), 8 eq. of TCEP (0.1 M), and 6 eq. of tris(3-hydroxy-propyltriazolylmethyl)amine (THPTA) in $H_2O$ (50 mM) was degased and treated as described for MP. Then, 1.5 eq. of HBP—$N_3$ (10 mM) was added and the mixture was adjusted to pH 9. After the resin has been incubated with the reaction mixture it was degased and shook for 24 hrs. at RT. Following filtration and washing steps the resin was incubated with an aqueous ethylenediamine tetraacetic acid (EDTA, 10 mM) solution to remove copper residues.

Cleavage of the Peptides from the Resin

Complete and test cleavages of the peptides were performed with a TFA/scavenger (90:10 v/v) mixture by shaking at RT for 3 hrs. Purification of the peptides was performed by means of preparative reversed-phase high performance liquid chromatography (RP-HPLC). Peptides were identified with matrix assisted laser ionization time-of-flight (MALDI-ToF) mass spectrometry (MS) (Bruker Daltonics) and electrospray ionization (ESI) ion trap MS (Bruker Daltonics). Purity was analyzed with RP-HPLC. The measured m/z values were consistent with the calculated molecular weights. Finally, the prepared peptides were obtained with a purity≥90%.

Biotin Enzyme-Linked Immunosorbent Assay (ELISA)

Titanium foil (Sigma Aldrich, thickness: 0.127 mm) was cut to round pieces (area=0.43 $cm^2$) and etched in $H_2SO_4$ (30%)/$H_2O_2$ (1:1 v/v) for 7 min. Following washing steps with water and TBS buffer (50 mM tris(hydroxymethyl)-aminomethane (Tris), 150 mM NaCl, pH 7.6) the titanium slices were incubated with various concentrations of biotinylated peptides in TBS buffer dissolved for 2 hrs. at RT. Subsequently, the coated slices were washed 5 times with TBS-T buffer (50 mM Tris, 150 mM NaCl, 0.1% Tween 20, pH 7.6) and transferred to new reaction vessels. The following biotin ELISA was performed in accordance with Hassert et al.[3] Zero reading values were obtained with uncoated titanium slices and subtracted from the generated values (absorption per $cm^2$). The obtained data points were non-linearly fitted with GraphPad Prism 5 software (GraphPadInc.). Error bars are represented as standard error of the mean (SEM) from at least 2 independent experiments.

Stability Test by Means of the Biotin ELISA

Titanium slices were etched as described and incubated overnight with 1 µM of peptide solutions in TBS buffer at RT. Subsequently, the coated slices were washed 5 times with TBS-T buffer and transferred to new reaction vessels. Thereafter, the titanium slices were incubated with cell supernatant (of SaOS-2 cells after 2 days of cell cultivation) at 37° C. for certain times. To detect unbound, biotinylated peptide on the surface the titanium slices were washed 4 times with TBS-T and once with TBS and the biotin ELISA was performed as described. Zero reading values were obtained by uncoated titanium slices and subtracted from the generated data. The obtained measuring values were normalized to the value measured at 0 min. Error bars are represented as standard error of the mean (SEM) from at least 2 independent experiments (double determination).

Cell Cultivation

SaOS-2 cells (osteogenic sarcoma) were cultivated in humid atmosphere at 37° C. and 5% $CO_2$ in McCoy's 5A medium with 15% heat-inactivated fetal calf serum (FCS), 1% (v/v) glutamine and 1% (v/v) penicillin/streptomycin.

Preparation of the Titanium Slices for Cellular Assays

Titanium foil was stamped and etched as already described. Following washing steps with water and PBS buffer (Dulbeccos phosphate) the titanium slices were sterilized with 70% ethanol/water (v/v) in an ultrasonic bath for 15 min. After having washed twice with PBS buffer the titanium slices were incubated overnight in a 48-well plate at RT with 300 µL of 1 µM of a peptide solution in PBS, PBS (negative control), and fibronectin in PBS (25 µg/mL, positive control).

Cell Adhesion Assay

Coated titanium slices (48-well plate) were washed twice with PBS. SaOS-2 cells were re-suspended in medium without FCS. Thereafter, the cells were sown on the coated titanium slices (50,000-90,000 cells per well, in this range we didn't find any influence on the cell plane for respective coating). Following adhesion for 6 hrs. the slices were washed with PBS and the cells were fixed with 4% paraformaldehyde in PBS for 30 min. Subsequently, the adhered cells were washed and permeabilized with 1% Triton X-100 in PBS for 1 min. Thereafter, the cells were dyed with phalloidin-tetramethylrhodamine isothiocyanate (phalloidin-TRITC) and HOECHST 33342 (both Sigma Aldrich). For fluorescence microscopy (Axio Observer microscope, Zeiss) the slices were attached to slides. For each slice (triplicate) 3 representative images at 20 fold and 10 fold magnification were made. Then, the average cell plane was determined by edging (Software Axio Vision 4.8, Zeiss) each single cell on one representative image (20 fold) each of each triplicate. The determined values were summarized from 3 independent experiments and represented as mean±SEM. To determine the cell number, three 10 fold magnified images were evaluated by means of ImageJ software and normalized to titanium=1, n≥3.

Immunolabelling

Cells (40,000 per well) were sown onto coated and washed titanium slices as already described. After 1 d of cell adhesion the slices were washed twice with PBS. All of the following washing steps were performed with 0.05% (v/v) Tween-20 in PBS. Thereafter, the cells were fixed and permeabilized as already described. To block unspecific interactions the slices were incubated with 1% bovine serum albumin (BSA) in PBS for 40 min. Subsequently, the cells were incubated with a murine monoclonal antibody against vinculin (Millipore, staining kit, 1:200) for 1 hr. at RT. Thereafter, the cells were washed and labeled with phalloidin-TRITC and a fluoresceinisothiocyanate (FITC) conjugated goat anti-mouse antibody (Millipore, 1:100) in 1% (v/v) BSA in PBS for 2 hr. Following a further washing step the nucleus was dyed with 4',6-diamidino-2-phenylindol (DAPI, Millipore) in PBS for 15 min. Before the slices were attached to slides they were washed three times for 10 min. each. Fluorescence microscopy was performed on an Axio Observer microscope and an ApoTome Imaging System (Zeiss).

Viability Assay

Cells were sown onto coated and washed titanium slices in FCS-free medium in a 96-well plate. After one day the medium was replaced by FCS-containing medium. On day 3 20 µL of CellTiderBlue® (Promega) were added to each well. After 2 hrs. of incubation the reaction of resazurin to resorufin was determined by means of fluorescence intensity measurement at 560Ex/590Em nm. The measured values (mean±SEM) were evaluated from 4 independent experiments performed in triplicate.

Proliferation Assay

Cells were sown onto coated and washed titanium slices in FCS-free medium in a 96-well plate. After one day the medium was replaced by FCS-containing medium. On day 2 bromodeoxyuridine (BrdU) was added to each well for labelling (colorimetric Cell Proliferation kit, Roche). After 24 hrs. of incorporation of the label the cells were washed and fixed. Subsequently, it was incubated with a peroxidase (POD) conjugated anti-BrdU antibody. Binding of the antibody was detected with the addition of a 3,3',5,5'-tetramethylbenzidine (TMB) solution and $H_2O_2$(Calbiochem). The enzymatic reaction was stopped with 1 M HCl. The measured values (mean±SEM) were evaluated from 4 independent experiments performed in triplicates and normalized to uncoated titanium.

Additional Information

Cleavage of Peptides from the Solid Phase—Details

The following scavenger mixtures were used: TIS (triisopropylsilane)/$H_2O$ (1:1 v/v) for HBP, thioanisole/ethanedithiol or thioanisole/thiocresol (1:1 v/v) for c[RGDfK(dienophile)] and all mussel peptides, for MP diene $H_2O$ was used. Then, the peptides were precipitated in ice-cold ethyl ether and washed. The resulting pellet was dissolved and subsequently lyophilized.

Purification of the peptides was made on the following preparative RP-HPLC column: Phenomenex Jupiter Proteo C18 column (90 Å/4 µm, 22 mm×250 mm). Linear gradients of Eluent B in Eluent A (A: 0.1% TFA in $H_2O$, B: 0.08% TFA in ACN) were used. The purities of the peptides were determined by means of the following columns: Varian VariTide RPC (200 Å, 6 µm), Phenomenex Jupiter Proteo C18 (90 Å/4 µm), and C18 (300 Å, 5 µm)) with linear gradients of Eluent A and B (A: 0.1% TFA in $H_2O$, B: 0.08% TFA in ACN).

Analysis of the Synthesized Peptides

TABLE 1

Analytics of the purified, isolated Peptides

| Peptide | Sequence | M [Da] | [M+H]$^+$ | Elution (%ACN)$^a$ | Purity [%] |
|---|---|---|---|---|---|
| MP | C-Peg-Y*-K-Y*-Peg-G*-βA-NH$_2$ (SEQ ID NO: 8) | 1178.5 | 1179.6 | 33 | >95 |
| bio-MP | Bio-X-X-C-Peg-Y*-K-Y*-Peg-G*-βA-NH$_2$ (SEQ ID NO: 3) | 1631.0 | 1631.9 | 41 | >95 |
| bio-(+) mefp-1 | Bio-X-X-A-K-P*-S-Y*-P*-P*-T-Y*-K-NH$_2$ (SEQ ID NO: 4) | 1681.7 | 1682.6 | 34 | >95 |
| bio-(−) mefp-1 | P*-T-Y-K-NH$_2$ (SEQ ID NO: 5) | 1649.9 | 1651.0 | 33 | >95 |
| MP-Ahx | C-X-Y*-K-Y*-X-G-βA-NH$_2$ (SEQ ID NO: 6) | 998.5 | 999.6 | 32 | >95 |
| RGD | c[RGDfK (dienophile)] | 915.5 | 916.5 | 44 | >95 |
| MP-RGD | C-Peg-Y*-K(c[RGDfK])-Y*-Peg-G*-βA-NH$_2$ | 2349.1 | 2350.1 | 36 $^b$ | >90 |
| N$_3$-HBP | K(N$_3$)-FHRRIKA-NH$_2$ (SEQ ID NO: 7) | 1079.7 | 1080.8 | 32 $^b$ | >95 |
| MP-HBP | C-Peg-Y*-K-Y*-Peg-G*(K(N$_3$)-FHRRIKA-NH$_2$)-βA-NH$_2$ | 2258.5 | 2259.2 | 32 $^c$ | >95 |
| MP-RGD-HBP | C-Peg-Y*-K(c[RGDfK])-Y*-Peg-G*(K(N$_3$)-FHRRIKA-NH$_2$)-βA-NH$_2$ | 3428.8 | 3429.8 | 32 $^b$ | >90 |

Identification was detected by means of MALDI-ToF MS (Bruker, Daltonics).
Peptide purity was determined with two different HPLC systems (different column and gradient);
$^a$Phenomenex Jupiter Proteo C18 (300 Å, 5 µm),
$^b$ Phenomenex Jupiter Proteo C18 (90 Å, 4 µm), and
$^c$ Varian VariTide RPC (200 Å, 6 µm) PEG (polyethylene glycol),
Y* (L-3,4-dihydroxyphenylalanine),
G* (propargylglycine),
X (amino hexanoic acid),
Bio (biotin),
P* (4-hydroxyproline)

Cell Adhesion

Figure 6:
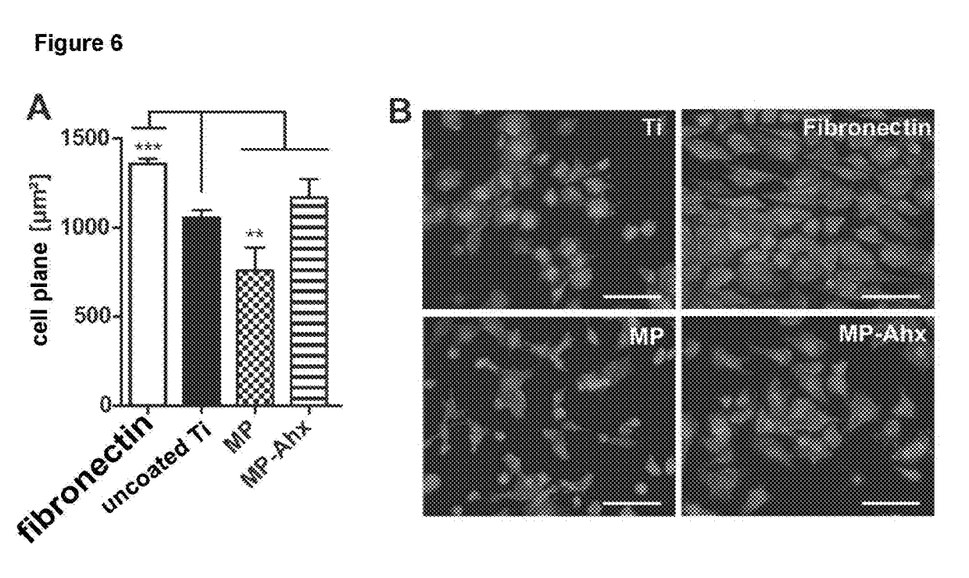
FIG. 6: Cell propagation on the peptide coatings (A) average cell plane (standard error of the mean. n=3) (B) Fluorescence microscopy of SaOS-2 cells after 6 h of adhesion on the peptide coatings. The actin cytoskeleton is red colored and the nucleus is blue, scale: 100 μm.

To test whether the cell repellent properties were mediated by PEG, PEG in MP was replaced by amino hexanoic acid and tested with SaOS-2 cells as described (see, FIG. 6).

REFERENCES (1) Kumar, V.; Aldrich, J. V. *Org Lett* 2003, 5, 613.
(2) Prime, K. L.; Whitesides, G. M. *J. Am. Chem. Soc.* 1993, 115, 10714.
(3) Hassert, R.; Pagel, M.; Ming, Z.; Haupl, T.; Abel, B.; Braun, K.; Wiessler, M.; Beck-Sickinger, A. G. *Bioconjug. Chem.* 2012, 23, 2129.
(4) Taylor, C. M.; Weir, C. A. *J. Org. Chem.* 2000, 65, 1414.
(5) Wischerhoff, E.; Uhlig, K.; Lankenau, A.; Borner, H. G.; Laschewsky, A.; Duschl, C.; Lutz, J. F. *Angew. Chem. Int. Ed.* 2008, 47, 5666.
(6) Geiger, B.; Spatz, J. P.; Bershadsky, A. D. *Nat. Rev. Mol. Cell. Bio.* 2009, 10, 21.
(7) Pipkorn, R.; Waldeck, W.; Didinger, B.; Koch, M.; Mueller, G.; Wiessler, M.; Braun, K. *J. Pept. Sci.* 2009, 15, 235.
(8) Bohme, D.; Beck-Sickinger, A. G. *Chemmedchem* 2015, 10, 804.

The invention claimed is:

1. A peptide comprising (i) a main chain comprising at least one L-3,4-dihydroxyphenylalanine (DOPA), (ii) at least one integrin binding peptide, and (iii) at least one heparin binding peptide, wherein the main chain comprises the sequence Cys PEG-DOPA Lys-DOPA-PEG-L-propargylglycine-β-Ala-NH$_2$ (SEQ ID NO:2).

2. The peptide according to claim 1, wherein the main chain is derived from a protein from the mussel *Mytilus edulis*.

3. The peptide according to claim 1, wherein the at least one integrin binding peptide comprises the amino acid sequence Arg-Gly-Asp.

4. The peptide according to claim 3, wherein the at least one integrin binding peptide comprises the amino acid sequence c[Arg-Gly-Asp-D-Phe-Lys].

5. The peptide according to claim 1, wherein the at least one heparin binding peptide comprises the amino acid sequence Phe-His-Arg-Arg-Ile-Lys-Ala (SEQ ID NO:1).

6. A coating for metal surfaces comprising a peptide according to claim 1.

7. The coating according to claim 6, wherein the metal surface substantially consists of titanium.

8. The coating according to claim 7, wherein the metal surface is part of an implant that is for implantation into a human or animal body.

9. The coating according to claim 8, wherein the implant is selected from the group consisting of dental implants and orthopaedic implants.

10. A coated metal surface that can be obtained by reacting a peptide according to claim 1 with a metal surface.

11. The coated metal surface according to claim 10, wherein the metal surface comprises titanium.

12. The coated metal surface according to claim 10, wherein the metal surface is part of an implant that is for implantation into a human or animal body.

13. The coated metal surface according to claim 12, wherein the implant is selected from the group consisting of dental implants and orthopaedic implants.

14. A coated implant that can be obtained by reacting a peptide according to claim 1 with an implant.

15. The coated implant according to claim 14, wherein the implant is selected from the group consisting of dental implants and orthopaedic implants.

16. A peptide comprising (i) a main chain comprising at least one L-3,4-dihydroxyphenylalanine (DOPA), (ii) at least one integrin binding peptide, and (iii) at least one heparin binding peptide, that can be obtained by a combination of solid phase synthesis and click chemistry.

* * * * *

SEQUENCE LISTING

<160> NUMBER OF SEQ ID NOS: 8

<210> SEQ ID NO 1
<211> LENGTH: 7
<212> TYPE: PRT
<213> ORGANISM: Artificial Sequence
<220> FEATURE:
<223> OTHER INFORMATION: heparin binding sequence

<400> SEQUENCE: 1

Phe His Arg Arg Ile Lys Ala
1               5

<210> SEQ ID NO 2
<211> LENGTH: 8
<212> TYPE: PRT
<213> ORGANISM: Artificial Sequence
<220> FEATURE:
<223> OTHER INFORMATION: main chain, derived from a protein from Mytilus edulis

```
<220> FEATURE:
<221> NAME/KEY: MISC_FEATURE
<222> LOCATION: (2)..(2)
<223> OTHER INFORMATION: Xaa is amino-PEG-acid, preferably amino-PEG3-
      acid (-HN-CH2-CH2-O-CH2-CH2-O-CH2-CH2-O-CH2-CH2-CO-)
<220> FEATURE:
<221> NAME/KEY: MISC_FEATURE
<222> LOCATION: (3)..(3)
<223> OTHER INFORMATION: Xaa is L-3,4-dihydroxyphenylalanine (DOPA)
<220> FEATURE:
<221> NAME/KEY: MISC_FEATURE
<222> LOCATION: (5)..(5)
<223> OTHER INFORMATION: Xaa is L-3,4-dihydroxyphenylalanine (DOPA)
<220> FEATURE:
<221> NAME/KEY: MISC_FEATURE
<222> LOCATION: (6)..(6)
<223> OTHER INFORMATION: Xaa is amino-PEG-acid, preferably amino-PEG3-
      acid (-HN-CH2-CH2-O-CH2-CH2-O-CH2-CH2-O-CH2-CH2-CO-)
<220> FEATURE:
<221> NAME/KEY: MISC_FEATURE
<222> LOCATION: (7)..(7)
<223> OTHER INFORMATION: Xaa is L-propargylglycine
<220> FEATURE:
<221> NAME/KEY: MOD_RES
<222> LOCATION: (8)..(8)
<223> OTHER INFORMATION: AMIDATION, bAla

<400> SEQUENCE: 2

Cys Xaa Xaa Lys Xaa Xaa Xaa Xaa
1               5

<210> SEQ ID NO 3
<211> LENGTH: 10
<212> TYPE: PRT
<213> ORGANISM: Artificial Sequence
<220> FEATURE:
<223> OTHER INFORMATION: bio-MP
<220> FEATURE:
<221> NAME/KEY: MOD_RES
<222> LOCATION: (1)..(1)
<223> OTHER INFORMATION: Acp
<220> FEATURE:
<221> NAME/KEY: MISC_FEATURE
<222> LOCATION: (1)..(1)
<223> OTHER INFORMATION: N-terminal biotinylation
<220> FEATURE:
<221> NAME/KEY: MOD_RES
<222> LOCATION: (2)..(2)
<223> OTHER INFORMATION: Acp
<220> FEATURE:
<221> NAME/KEY: MISC_FEATURE
<222> LOCATION: (4)..(4)
<223> OTHER INFORMATION: Xaa is amino-PEG3-acid
      (-HN-CH2-CH2-O-CH2-CH2-O-CH2-CH2-O-CH2-CH2-CO-)
<220> FEATURE:
<221> NAME/KEY: MISC_FEATURE
<222> LOCATION: (5)..(5)
<223> OTHER INFORMATION: Xaa is L-3,4-dihydroxyphenylalanine
<220> FEATURE:
<221> NAME/KEY: MISC_FEATURE
<222> LOCATION: (7)..(7)
<223> OTHER INFORMATION: Xaa is L-3,4-dihydroxyphenylalanine
<220> FEATURE:
<221> NAME/KEY: MISC_FEATURE
<222> LOCATION: (8)..(8)
<223> OTHER INFORMATION: Xaa is amino-PEG3-acid
      (-HN-CH2-CH2-O-CH2-CH2-O-CH2-CH2-O-CH2-CH2-CO-)
<220> FEATURE:
<221> NAME/KEY: MISC_FEATURE
<222> LOCATION: (9)..(9)
<223> OTHER INFORMATION: Xaa is propargylglycine
<220> FEATURE:
<221> NAME/KEY: MOD_RES
<222> LOCATION: (10)..(10)
<223> OTHER INFORMATION: AMIDATION, bAla

<400> SEQUENCE: 3
```

```
Xaa Xaa Cys Xaa Xaa Lys Xaa Xaa Xaa Xaa
1               5                   10

<210> SEQ ID NO 4
<211> LENGTH: 12
<212> TYPE: PRT
<213> ORGANISM: Artificial Sequence
<220> FEATURE:
<223> OTHER INFORMATION: bio-(+)mefp-1
<220> FEATURE:
<221> NAME/KEY: MOD_RES
<222> LOCATION: (1)..(1)
<223> OTHER INFORMATION: Acp
<220> FEATURE:
<221> NAME/KEY: MISC_FEATURE
<222> LOCATION: (1)..(1)
<223> OTHER INFORMATION: N-terminal biotinylation
<220> FEATURE:
<221> NAME/KEY: MOD_RES
<222> LOCATION: (2)..(2)
<223> OTHER INFORMATION: Acp
<220> FEATURE:
<221> NAME/KEY: MOD_RES
<222> LOCATION: (5)..(5)
<223> OTHER INFORMATION: 4Hyp
<220> FEATURE:
<221> NAME/KEY: MISC_FEATURE
<222> LOCATION: (7)..(7)
<223> OTHER INFORMATION: Xaa is L-3,4-dihydroxyphenylalanine
<220> FEATURE:
<221> NAME/KEY: MOD_RES
<222> LOCATION: (8)..(8)
<223> OTHER INFORMATION: 4Hyp
<220> FEATURE:
<221> NAME/KEY: MOD_RES
<222> LOCATION: (9)..(9)
<223> OTHER INFORMATION: 4Hyp
<220> FEATURE:
<221> NAME/KEY: MISC_FEATURE
<222> LOCATION: (11)..(11)
<223> OTHER INFORMATION: Xaa is L-3,4-dihydroxyphenylalanine
<220> FEATURE:
<221> NAME/KEY: MOD_RES
<222> LOCATION: (12)..(12)
<223> OTHER INFORMATION: AMIDATION

<400> SEQUENCE: 4

Xaa Xaa Ala Lys Xaa Ser Xaa Xaa Xaa Thr Xaa Lys
1               5                   10

<210> SEQ ID NO 5
<211> LENGTH: 12
<212> TYPE: PRT
<213> ORGANISM: Artificial Sequence
<220> FEATURE:
<223> OTHER INFORMATION: bio-(-)mefp-1
<220> FEATURE:
<221> NAME/KEY: MOD_RES
<222> LOCATION: (1)..(1)
<223> OTHER INFORMATION: Acp
<220> FEATURE:
<221> NAME/KEY: MISC_FEATURE
<222> LOCATION: (1)..(1)
<223> OTHER INFORMATION: N-terminal biotinylation
<220> FEATURE:
<221> NAME/KEY: MOD_RES
<222> LOCATION: (2)..(2)
<223> OTHER INFORMATION: Acp
<220> FEATURE:
<221> NAME/KEY: MOD_RES
<222> LOCATION: (5)..(5)
<223> OTHER INFORMATION: 4Hyp
<220> FEATURE:
<221> NAME/KEY: MOD_RES
<222> LOCATION: (8)..(8)
```

```
<223> OTHER INFORMATION: 4Hyp
<220> FEATURE:
<221> NAME/KEY: MOD_RES
<222> LOCATION: (9)..(9)
<223> OTHER INFORMATION: 4Hyp
<220> FEATURE:
<221> NAME/KEY: MOD_RES
<222> LOCATION: (12)..(12)
<223> OTHER INFORMATION: AMIDATION

<400> SEQUENCE: 5

Xaa Xaa Ala Lys Pro Ser Tyr Pro Pro Thr Tyr Lys
1               5                   10

<210> SEQ ID NO 6
<211> LENGTH: 8
<212> TYPE: PRT
<213> ORGANISM: Artificial Sequence
<220> FEATURE:
<223> OTHER INFORMATION: MP-Ahx
<220> FEATURE:
<221> NAME/KEY: MOD_RES
<222> LOCATION: (2)..(2)
<223> OTHER INFORMATION: Acp
<220> FEATURE:
<221> NAME/KEY: MISC_FEATURE
<222> LOCATION: (3)..(3)
<223> OTHER INFORMATION: Xaa is L-3,4-dihydroxyphenylalanine
<220> FEATURE:
<221> NAME/KEY: MISC_FEATURE
<222> LOCATION: (5)..(5)
<223> OTHER INFORMATION: Xaa is L-3,4-dihydroxyphenylalanine
<220> FEATURE:
<221> NAME/KEY: MOD_RES
<222> LOCATION: (6)..(6)
<223> OTHER INFORMATION: Acp
<220> FEATURE:
<221> NAME/KEY: MISC_FEATURE
<222> LOCATION: (7)..(7)
<223> OTHER INFORMATION: Xaa is propargylglycine
<220> FEATURE:
<221> NAME/KEY: MOD_RES
<222> LOCATION: (8)..(8)
<223> OTHER INFORMATION: AMIDATION, bAla

<400> SEQUENCE: 6

Cys Xaa Xaa Lys Xaa Xaa Xaa Xaa
1               5

<210> SEQ ID NO 7
<211> LENGTH: 8
<212> TYPE: PRT
<213> ORGANISM: Artificial Sequence
<220> FEATURE:
<223> OTHER INFORMATION: N3-HBP
<220> FEATURE:
<221> NAME/KEY: MISC_FEATURE
<222> LOCATION: (1)..(1)
<223> OTHER INFORMATION: Xaa is azidolysine (N3-lysine)
<220> FEATURE:
<221> NAME/KEY: MOD_RES
<222> LOCATION: (8)..(8)
<223> OTHER INFORMATION: AMIDATION

<400> SEQUENCE: 7

Xaa Phe His Arg Arg Ile Lys Ala
1               5

<210> SEQ ID NO 8
<211> LENGTH: 8
<212> TYPE: PRT
<213> ORGANISM: Artificial Sequence
<220> FEATURE:
```

```
<223> OTHER INFORMATION: MP
<220> FEATURE:
<221> NAME/KEY: MISC_FEATURE
<222> LOCATION: (2)..(2)
<223> OTHER INFORMATION: Xaa is amino-PEG3-acid
      (-HN-CH2-CH2-O-CH2-CH2-O-CH2-CH2-O-CH2-CH2-CO-)
<220> FEATURE:
<221> NAME/KEY: MISC_FEATURE
<222> LOCATION: (3)..(3)
<223> OTHER INFORMATION: Xaa is L-3,4-dihydroxyphenylalanine
<220> FEATURE:
<221> NAME/KEY: MISC_FEATURE
<222> LOCATION: (5)..(5)
<223> OTHER INFORMATION: Xaa is L-3,4-dihydroxyphenylalanine
<220> FEATURE:
<221> NAME/KEY: MISC_FEATURE
<222> LOCATION: (6)..(6)
<223> OTHER INFORMATION: Xaa is amino-PEG3-acid
      (-HN-CH2-CH2-O-CH2-CH2-O-CH2-CH2-O-CH2-CH2-CO-)
<220> FEATURE:
<221> NAME/KEY: MISC_FEATURE
<222> LOCATION: (7)..(7)
<223> OTHER INFORMATION: Xaa is propargylglycine
<220> FEATURE:
<221> NAME/KEY: MOD_RES
<222> LOCATION: (8)..(8)
<223> OTHER INFORMATION: AMIDATION, bAla

<400> SEQUENCE: 8

Cys Xaa Xaa Lys Xaa Xaa Xaa Xaa
1               5
```

UNITED STATES PATENT AND TRADEMARK OFFICE
CERTIFICATE OF CORRECTION

PATENT NO. : 10,787,485 B2
APPLICATION NO. : 15/759055
DATED : September 29, 2020
INVENTOR(S) : Annette Beck-Sickinger et al.

It is certified that error appears in the above-identified patent and that said Letters Patent is hereby corrected as shown below:

On the Title Page

The name of the Assignee in item (73) is incorrect. Item (73) should read Universität Leipzig.

In the Claims

In Claim 1, Column 21, Lines 36-37, SEQ ID NO:2 "Cys - PEG – DOPA - Lys – DOPA – PEG – L-Propargylglycine - ß-Ala - NH2" incorrectly appears as "Cys PEG – DOPA Lys – DOPA – PEG – L-Propargylglycine - ß-Ala - NH2".

Signed and Sealed this
Twenty-seventh Day of October, 2020

Andrei Iancu
*Director of the United States Patent and Trademark Office*